United States Patent [19]

Berg et al.

[11] Patent Number: 5,094,724

[45] Date of Patent: Mar. 10, 1992

[54] SEPARATION OF METHYLENE CHLORIDE FROM THE LOWER FORMATES BY EXTRACTIVE DISTILLATION

[75] Inventors: Lloyd Berg, 1314 South Third Ave., Bozeman, Mont. 59715; Zuyin Yang, Bozeman, Mont.

[73] Assignee: Lloyd Berg, Bozeman, Mont.

[21] Appl. No.: 687,507

[22] Filed: Apr. 19, 1991

[51] Int. Cl.$^5$ .................. B01D 3/40; C07C 17/38
[52] U.S. Cl. .................................. 203/57; 203/60; 203/62; 203/63; 203/64; 560/248; 570/262
[58] Field of Search .................. 203/57, 60, 62, 63, 203/64; 570/262; 560/248

[56] References Cited

U.S. PATENT DOCUMENTS

| | | | |
|---|---|---|---|
| 2,865,955 | 12/1958 | Ascherl et al. | 560/248 |
| 3,350,416 | 10/1967 | Binning et al. | 560/248 |
| 3,431,181 | 3/1969 | Bouniot | 560/248 |
| 3,848,007 | 11/1974 | Forlano | 570/262 |
| 3,951,756 | 4/1976 | Dirks et al. | 560/248 |
| 4,036,703 | 7/1977 | LeRoi et al. | 203/60 |
| 4,083,931 | 4/1978 | Lee | 560/248 |
| 4,121,978 | 10/1978 | Becuwe | 203/60 |

FOREIGN PATENT DOCUMENTS

| | | | |
|---|---|---|---|
| 3135280 | 3/1983 | Fed. Rep. of Germany | 560/248 |
| 142183 | 6/1980 | German Democratic Rep. | 203/64 |

Primary Examiner—Wilbur Bascomb, Jr.

[57] ABSTRACT

Methylene chloride cannot be completely separated from methyl formate or ethyl formate by conventional distillation or rectification because of the minimum boiling azeotrope. Methylene chloride can be readily separated from methyl formate or ethyl formate by extractive distillation. Typical effective agents are: for methyl formate, n-butyl acetate and 3-hexanone; for ethyl formate, isobornyl acetate and 2-heptanone.

2 Claims, No Drawings

SEPARATION OF METHYLENE CHLORIDE FROM THE LOWER FORMATES BY EXTRACTIVE DISTILLATION

FIELD OF THE INVENTION

This invention relates to a method for separating methylene chloride from methyl formate or ethyl formate using certain organic compounds as the agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Centigrade degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

Methylene chloride, B.P.=40° C. forms a minimum boiling azeotrope with methyl formate, B.P.=32° C. at 31° C. containing 20% methylene chloride. Methylene chloride forms a minimum boiling azeotrope with ethyl formate, B.P.=54° C. at 39.5° C. containing 77% methylene chloride. The methylene chloride - formate azeotropes are impossible to separate by distillation because the relative volatility of an azeotrope is 1.0. Extractive distillation would be an attractive method of effecting the separation of methylene chloride from these formates if agents can be found that (1) will enhance the relative volatility between methylene chloride and these formates ans (2) are easy to recover, that is, form no azeotrope with methylene chloride, methyl formate or ethyl formate and boil sufficiently above these three compounds to make separation by rectification possible with only a few theoretical plates.

Extractive distillation typically requires the addition of an equal amount to twice as much extractive agent as the methylene chloride - formate on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required in azeotropic distillation.

Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. We recommend twenty Centigrade degrees or more difference. It is also desirable that the extractive agent be miscible with the methylene chloride and the formates otherwise it will form a two phase azeotrope with it and some other method of separation will have to be employed.

TABLE 1

Effect of Relative Volatility on the Separation of Methylene Chloride from Formates at 99% Purity.

| Relative Volatility | Theoretical Plates | Actual Plates, 75% Efficiency | Actual Plates, 75% Eff., Min. Reflux |
|---|---|---|---|
| 1.2 | 50 | 67 | 87 |
| 1.3 | 35 | 47 | 61 |
| 1.4 | 27 | 36 | 47 |
| 1.5 | 23 | 31 | 40 |
| 1.6 | 20 | 27 | 35 |
| 1.7 | 17 | 23 | 29 |

The advantage of employinng an effective extractive distillation agent for this separation is shown in Table 1. When ordinary rectification is used, 87 usual plates of 75% efficiency are required at minimum reflux ratio to separate methylene chloride from the formates in 99% purity. If extractive distillation is employed with an agent that converts the relative volatility to 1.7, only 29 plates are required.

OBJECTIVE OF THE INVENTION

The objects of this invention are to provide a process or method of azeotropic or extractive distillation that will enhance the relative volatility of methylene chloride to methyl formate or ethyl formate in their separation in a rectification column. It is a further object of this invention to identify organic compounds that are stable, can be separated from the methylene chloride or formate by rectification with relatively few plates and can be recycled to the extractive distillation column with little decomposition.

SUMMARY OF THE INVENTION

The objects of this invention are provided by a process for the separation of methylene chloride from methyl formate or ethyl formate which entails the use of certain organic compounds as the agent in extractive distillation.

DETAILED DESCRIPTION OF THE INVENTION

We have discovered that certain organic compounds will effectively increase the relative volatility between methylene chloride and methyl formate or ethyl formate and permit the separation of methylene chloride from methyl formate or ethyl formate by rectification when employed as the agent in extractive distilation. Table 2 lists the agents that we have found to be effective extractive distillation agents to recover methylene chloride from methyl formate. The data in Tables 2, 4 and 5 was obtained in a vapor-liquid equilibrium still. In every case, the starting mixture was the methylene chloride - methyl formate or ethyl formate azeotrope. The relative volatilities are listed for each the agents investigated. The compounds which are effective extractive distillation agents to remove methylene chloride from methyl formate are methyl acetate, ethyl acetate, isopropyl acetate, n-propyl acetate, n-butyl acetate, isobutyl acetate, isoamyl acetate, n-amyl acetate, ethylene glycol methyl ether acetate, 4-methyl-2-pentanone, 3-pentanone, mesityl oxide, 3-hexanone, 2-hexanone, ethyl butyl ketone, 2-methyl pentanone, 3,3-dimethyl-2-butanone, methyl isoamyl ketone, propylene glycol dimethyl ether and 3-methyl-1-butanol.

n-Butyl acetate whose relative volatility had been determined in the vapor-liquid equilibrium still was then evaluated in a glass perforated plate rectification column possessing 7.3 theoretical plates and the results listed in Table 3. After two hours of continuous operation a relative volatility for n-butyl acetate of 2.0 was obtained.

Table 4 lists the agents that we have found to be effective extractive distillation agents to recover methylene chloride from ethyl formate. They are n-butyl acetate, isobutyl acetate, n-amyl acetate, isoamyl acetate, hexyl acetate, isobornyl acetate, ethylene glycol ethyl ether acetate, 2-hexanone, mesityl oxide, 3,3-dimethyl-2-butanone, ethyl butyl ketone, 3-methyl-2-butanone, 3-hexanone, 2-heptanone, diisobutyl ketone, methyl isoamyl ketone, 2,4-pentanedione, diacetone alcohol, propoxypropanol, butoxypropanol, propylene glycol methyl ether, propyl butyrate, dibutyl ether, diethylene glycol t-butyl methyl ether, nitromethane, 1-nitropropane and 2-nitropropane.

Table 5 lists a number of compounds that proved to be ineffective as extractive distillation agents in the separation of methylene chloride from ethyl formate.

TABLE 2

Effective Agents for Separating
Methylene Chloride From Methyl Formate

| Compounds | Relative Volatility |
|---|---|
| Methyl acetate | 2.75 |
| Ethyl acetate | 1.7 |
| Isopropyl acetate | 2.3 |
| n-Propyl acetate | 1.85 |
| 4-Methyl-2-pentanone | 1.95 |
| 3-Pentanone | 2.0 |
| n-Butyl acetate | 2.0 |
| Isobutyl acetate | 1.8 |
| Mesityl oxide | 2.0 |
| 3-Hexanone | 2.0 |
| 2-Hexanone | 1.95 |
| 3-Methyl-1-butanol | 1.5 |
| Ethyl butyl ketone | 2.1 |
| 3,3-Dimethyl-2-butanone | 1.9 |
| 2-Methyl pentanone | 1.65 |
| Isoamyl acetate | 2.1 |
| n-Amyl acetate | 2.8 |
| Propylene glycol dimethyl ether | 1.8 |
| Ethylene glycol methyl ether acetate | 1.75 |
| Methyl isoamyl ketone | 1.8 |

TABLE 3

Data From Run Made In Rectification
Column - Methylene Chloride - Methyl Formate

| Agent | Column | Time hrs. | Weight % CH$_2$Cl$_2$ | Weight % MeForm | Relative Volatility |
|---|---|---|---|---|---|
| n-Butyl acetate | Overhead | 1 | 96.7 | 3.3 | 1.3 |
| | Bottoms | | 69.3 | 30.7 | |
| " | Overhead | 2 | 99.8 | 0.2 | 2.0 |
| | Bottoms | | 78.3 | 21.7 | |

Isobornyl acetate whose relative volatility had been determined in the vapor-liquid equilibrium still was then evaluated in the glass perforated plate rectification column possessing 7.3 theoretical plates and the results listed Table 6. After two hours of continuous operation, a relative volatility for isobornyl acetate of 1.4 was obtained.

THE USEFULNESS OF THE INVENTION

The usefulness or utility of this invention can be demonstrated by referring to the data presented in Tables 2 to 6. All of the successful agents show that methylene chloride can be separated from methyl formate or ethyl formate by extractive distillation in a rectification column and that the ease of separation as measured by relative volatility is considerable.

TABLE 4

Effective Agents For Separating
Methylene Chloride From Ethyl Formate

| Compounds | Relative Volatility |
|---|---|
| n-Butyl acetate | 1.25 |
| Isobutyl acetate | 1.35 |
| n-Amyl acetate | 1.3 |
| Isoamyl acetate | 1.35 |
| Ethylene glycol ethyl ether acetate | 1.7 |
| Isobornyl acetate | 1.55 |
| 2-Hexanone | 1.7 |
| Mesityl oxide | 1.25 |
| 3,3-Dimethyl-2-butanone | 1.25 |
| 3-Methyl-2-butanone | 1.55 |
| Ethyl butyl ketone | 1.25 |
| 3-Hexanone | 1.75 |
| 2-Heptanone | 1.65 |
| Diisobutyl ketone | 1.5 |
| Methyl isoamyl ketone | 1.5 |
| 2,4-Pentanedione | 1.7 |
| Diacetone alcohol | 3.3 |
| Propoxypropanol | 1.9 |
| Butoxypropanol | 1.5 |
| Propylene glycol methyl ether | 1.75 |
| Hexyl acetate | 1.25 |
| Propyl butyrate | 1.35 |
| Dibutyl ether | 1.9 |
| Diethylene glycol t-butyl methyl ether | 1.35 |
| Nitromethane | 2.5 |
| 1-Nitropropane | 1.8 |
| 2-Nitropropane | 2.0 |

TABLE 5

Ineffective Agents For Separating
Methylene Chloride From Ethyl Formate

| | |
|---|---|
| 3-Pentanone | Ethylene glycol methyl ether acetate |
| Vinyl butyl ether | Ethylene glycol butyl ether acetate |
| Nitroethane | 2-Methoxyethyl acetate |
| Methyl vinyl acetate | |

TABLE 6

| | Data From Run Made In Rectification Column - Methylene Chloride - Ethyl Formate | | | | |
|---|---|---|---|---|---|
| Agent | Column | Time hrs. | Weight % $CH_2Cl_2$ | Weight & EtFormate | Relative Volatility |
| Isobornyl acetate | Overhead | 1 | 97.2 | 2.8 | 1.23 |
|  | Bottoms |  | 88.6 | 11.4 |  |
| " | Overhead | 2 | 98.1 | 1.9 | 1.40 |
|  | Bottoms |  | 88.2 | 11.8 |  |

WORKING EXAMPLES

EXAMPLE 1

Eighty grams of the methylene chloride - methyl formate azeotrope and 30 grams of n-butyl acetate were charged to a vapor-liquid equilibrium still and refluxed for three hours. Analysis indicated a vapor composition of 89.9% methylene chloride, 10.1% methyl formate; a liquid composition of 79.5% methylene chloride, 20.5% methyl formate which is a relative volatility of methylene chloride to methyl formate of 2.3.

EXAMPLE 2

A solution comprising 40 grams of methylene chloride and 160 grams of methyl formate was placed in the stillpot of a 7.3 theoretical plate rectification column. When refluxing began, an extractive agent comprising n-butyl acetate was pumped into the column at a rate of 15 ml/min. The temperature of the extractive agent as it entered the column was 85° C. After establishing the feed rate of the extractive agent, the heat input to the methylene chloride - methyl formate in the stillpot was adjusted to give a total reflux rate of 40 ml/min. After two houss of operation, the overhead and bottoms samples of approximately two ml. were collected and analysed. The overhead analysis was 99.8% methylene chloride, 0.2% methyl formate and the bottoms analysis was 78.3% methylene chloride, 21.7% methyl formate. This gives an average relative volatility of 2.0 for each theoretical plate. This data is presented in Table 3.

EXAMPLE 3

Eighty grams of the methylene chloride - ethyl formate azeotrope and 30 grams of isobornyl acetate were charged to the vapor-liquid equilibrium still and refluxed for five hours. Analysis indicated a vapor composition of 94.5% methylene chloride, 5.5% ethyl formate; a liquid composition of 91.4% methylene chloride, 8.6% ethyl formate which is a relative volatility of methylene chloride to ethyl formate of 1.55.

EXAMPLE 4

A solution comprising 184 grams of methylene chloride and 16 grams of ethyl formate was placed in the stillpot of the 7.3 theoretical plate rectification column. When refluxing began, an extractive agent comprising isobornyl acetate was pumped into the column at a rate of 15 ml/min. The temperature of the extractive agent as it entered the column was 85° C. After establishing the feed rate of the extractive agent, the heat input to the methylene chloride - ethyl formate in the stillpot was adjusted to give a total reflux rate of 40 ml/min. After two hours of operation, the overhead analysis was 98.1% methylene chloride, 1.9% ethyl formate and the bottoms analysis was 88.2% methylene chloride, 11.8% ethyl formate. This gives an average relative volatility of 1.4 for each theoretical plate. This data is presented in Table 6.

We claim:

1. A method for recovering methylene chloride from a mixture of methylene chloride and methyl formate which comprises distilling a mixture of methylene chloride and methyl formate in the presence of about one part of an extractive agent per part of methylene chloride - methyl formate mixture, recovering the methylene chloride as overhead product and obtaining the methyl formate and the extractive agent from the stillpot, wherein said extractive agent consists of one material selected from the group consisting of methyl acetate, ethyl acetate, isopropyl acetate, n-propyl acetate, 4-methyl-2-pentanone, 3-pentanone, n-butyl acetate, isobutyl acetate, mesityl oxide, 3-hexanone, 2-hexanone, 3-methyl-1-butanol, ethyl butyl ketone, 3,3-dimethyl-2-butanone, 2-methyl pentanone, isoamyl acetate, n-amyl acetate, methyl isoamyl ketone, propylene glycol dimethyl ether and ethylene glycol methyl ether acetate.

2. A method for recovering methylene chloride from a mixture of methylene chloride and ethyl formate which comprises distilling a mixture of methylene chloride and ethyl formate in the presence of about one part of an extractive agent per part of methylene chloride - ethyl formate mixture, recovering the methylene chloride as overhead product and obtaining the ethyl formate and the extractive agent from the stillpot, wherein said extractive agent consists of one material selected from the group consisting of n-butyl acetate, isobutyl acetate, n-amyl acetate, isoamyl acetate, hexyl acetate, isobornyl acetate, ethylene glycol ethyl ether acetate, mesityl oxide, ethyl butyl ketone, 3,3-dimethyl-2-butanone, 3-methyl-2-butanone, 3-hexanone, 2-heptanone, diisobutyl ketone, methyl isoamyl ketone, 2,4-pentanedione, diacetone alcohol, propoxypropanol, butoxypropanol, propylene glycol methyl ether, propyl butyrate, dibutyl ether, diethylene glycol t-butyl methyl ether, nitromethane, 1-nitropropane and 2-nitropropane.

* * * * *